(12) United States Patent
Caye et al.

(10) Patent No.: US 6,472,488 B2
(45) Date of Patent: Oct. 29, 2002

(54) (THIO) (METH) ACRYLATE MONOMERS, INTERMEDIATE COMPOUNDS FOR THE SYNTHESIS OF THESE MONOMERS, POLYMERIZABLE COMPOSITIONS AND POLYMERS OBTAINED, AND THEIR OPTICAL AND OPHTHALMIC USES

(75) Inventors: Florence Caye, Saint-Avold; Michèle Sindt, Verny; Daniel Paquer, Vandoeuvre; Dorothée Jury, Chonas-l'Amballan; Michel Schneider, Le Ban-Saint-Martin; Jean-Luc Mieloszynski, Ars-sur-Moselle, all of (FR)

(73) Assignee: Essilor International Compagnie Generale D'Optique, Charenton Cedex (FR)

( * ) Notice: Subject to any disclaimer, the term of this patent is extended or adjusted under 35 U.S.C. 154(b) by 0 days.

(21) Appl. No.: 09/957,597

(22) Filed: Sep. 20, 2001

(65) Prior Publication Data

US 2002/0049289 A1 Apr. 25, 2002

Related U.S. Application Data

(62) Division of application No. 09/171,219, filed as application No. PCT/FR98/00254 on Feb. 10, 1998, now Pat. No. 6,307,062.

(30) Foreign Application Priority Data

Feb. 13, 1997 (FR) .......................................... 97 01687

(51) Int. Cl.$^7$ .............................................. C08F 128/02
(52) U.S. Cl. ........................... 526/286; 549/11; 549/18; 549/21; 549/22; 549/31; 549/32; 549/37
(58) Field of Search ........................ 526/286; 549/11, 549/18, 21, 22, 31, 32, 37

(56) References Cited

U.S. PATENT DOCUMENTS 5,807,906 A    9/1998 Bonvallot et al.

FOREIGN PATENT DOCUMENTS

| EP | 0 435 305 A2 | 12/1990 |
| EP | 0 435 306 A2 | 12/1990 |
| EP | 0 728 572 A2 | 8/1996 |

*Primary Examiner*—Bernard Lipman
(74) *Attorney, Agent, or Firm*—O'Keefe, Egan & Peterman, LLP

(57) ABSTRACT

Polymerizable compositions from novel monomers that correspond to the formula:

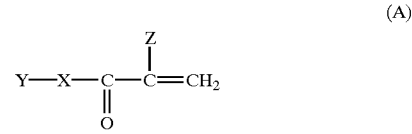

(A)

in which:

Z represents H or $CH_3$ and X represents O or S, and
Y is a 5- to 8-membered heterocycle consisting of hydrogen, carbon and sulphur atoms and at least two endocyclic sulphur atoms.

30 Claims, No Drawings

(THIO) (METH) ACRYLATE MONOMERS, INTERMEDIATE COMPOUNDS FOR THE SYNTHESIS OF THESE MONOMERS, POLYMERIZABLE COMPOSITIONS AND POLYMERS OBTAINED, AND THEIR OPTICAL AND OPHTHALMIC USES

This application is a divisional of application Ser. No. 09/171,219, filed Oct. 13, 1998, now U.S. Pat. No. 6,307,062, which is a §371 national filing of PCT application number PCT/FR98/00254, filed Feb. 10, 1998, which claims priority to French application Ser. No. 97/01687, filed Feb. 13, 1997.

The present invention relates, in general, to novel (thio)(meth)acrylate monomers, preferably mono(thio)(meth)acrylate monomers, which are useful for the formulation of polymerizable compositions leading to transparent homopolymers and copolymers that are suitable for optical and ophthalmic uses.

The polymerizable compositions according to the invention allow the manufacture of moulded articles made of transparent polymer, which is preferably thermoplastic, by polymerization in moulds or by injection-moulding.

The transparent polymers obtained, which have refractive indices of medium to high value, 1.54 or more, are particularly suitable for optical and ophthalmic uses.

Among the optical uses of the polymers according to the invention, mention may be made of wave guides and optical fibres.

Among the ophthalmic uses of these polymers, mention may be made of spectacle lenses and contact lenses.

In general, novel monomers according to the present invention are functional monomers of mono(thio)(meth)acrylate or mono- and di(meth)acrylate type bearing a 5- to 8-membered heterocycle consisting of hydrogen, carbon and sulphur atoms and having at least two endocyclic sulphur atoms. Preferably, the heterocycle is 6- or 7-membered, better still 6-membered. Also preferably, the number of endocyclic sulphur atoms is 2 or 3. The heterocycle can optionally be fused with a substituted or unsubstituted $C_5$–$C_8$ aromatic or polycyclanic ring, preferably a $C_6$–$C_7$ ring.

When the heterocycle of the functional monomers according to the invention contains 2 endocyclic sulphur atoms, these endocyclic sulphur atoms are preferably in positions 1–3 or 1–4 of the heterocycle. According to the invention, the monomer is preferably also a thio(meth)acrylate monomer. Lastly, the monomers according to the invention preferably have molar masses of between 150 and 400, preferably 150 and 350 and better still between 200 and 300.

More particularly, the novel functional monomers according to the invention correspond to the formula

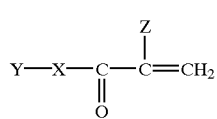
(A)

in which Z represents H or $CH_3$ (preferably $CH_3$) and X represents O or S, and when X represents S, Y represents a radical of formula:

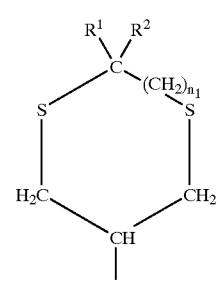
(a)

where $R^1$ and $R^2$ are chosen from H, alkyl radicals, preferably $C_1$–$C_4$ alkyl radicals and better still the $CH_3$ radical, or alternatively $R^1$ and $R^2$ together form a $(CH_2)_5$ radical, and $n_1$ is an integer from 0 to 2 inclusive, and when X represents O, Y represents the radical (a) defined above or a radical chosen from the radicals of formulae:

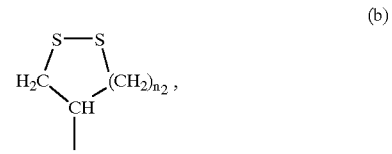
(b)

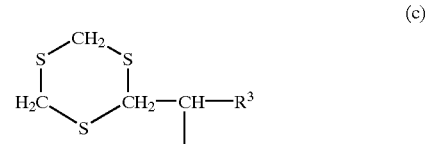
(c)

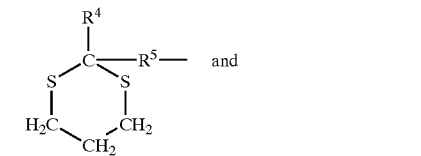
(d)

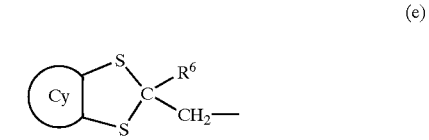
(e)

in which $n_2$ is equal to 1 or 2, $R^3$ represents H or an alkyl radical, preferably a $C_1$–$C_4$ alkyl radical and better still a $CH_3$ radical, $R^4$ represents H or an alkyl radical, preferably a $C_1$–$C_4$ alkyl radical and better still a $CH_3$ or $C_2H_5$ radical, and $R^5$ is a divalent radical chosen from the groups of the following formulae:

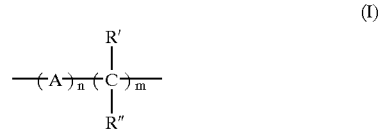
(I)

in which:
A denotes an aryl group, preferably a $C_6$–$C_{12}$ aryl group and better still a phenyl group, or an alkyl group, preferably a $C_1$–$C_6$ alkyl group,
R' and R" denote, independently of each other, H, an alkyl group, preferably a $C_1$–$C_6$ alkyl group, aryl, preferably phenyl, or R' or R" can be a group

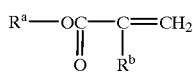

where $R^a$ is an alkylene group, preferably a $C_1$–$C_6$ alkylene group, in particular a —$CH_2$— group, and $R^b$ is H or $CH_3$, n takes the values 0 or 1 and $0 \leq m$ (integer $\leq 4$), and

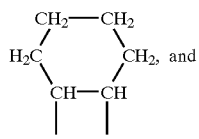

(II)

$R_6$ denotes H or $CH_3$, and

Cy denotes a substituted or unsubstituted aryl ring, preferably a phenyl, tolyl or norbornyl ring.

Preferably, $R^5$ is a divalent radical chosen from:

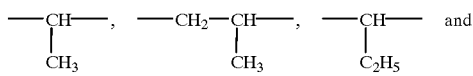

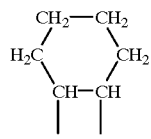

The monomers according to the invention which are particularly recommended are the thio(meth)acrylate monomers corresponding to the formula (A) above in which X represents a sulphur atom and Y is a radical of formula (a).

The monomers according to the invention can be prepared by various known synthetic processes.

Among the mono(thio)(meth)acrylic monomers which are preferred according to the invention, mention may be made of the monomers of formulae:

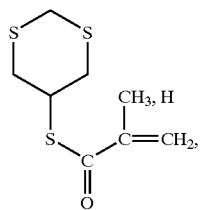
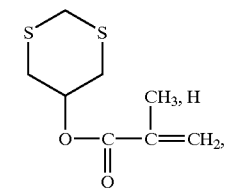
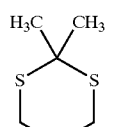
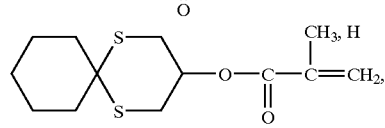

-continued

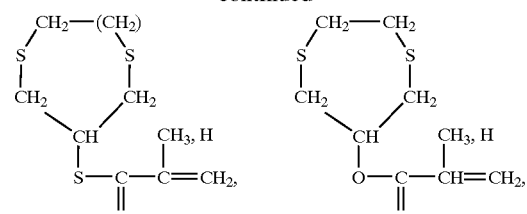
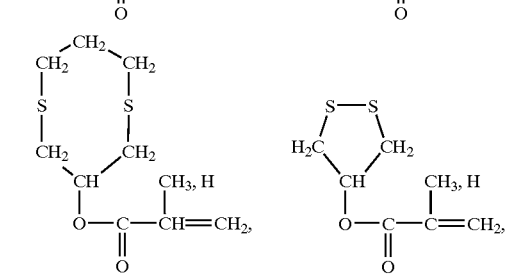
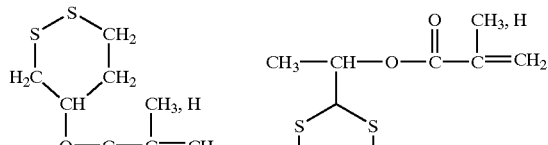
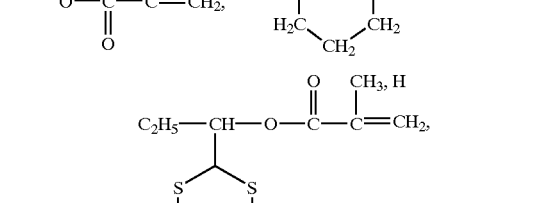
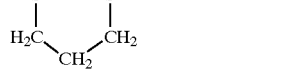
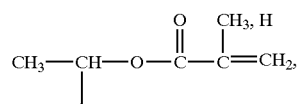
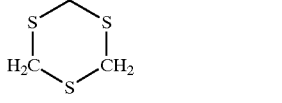
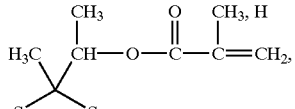
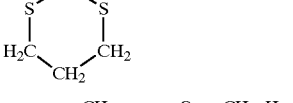
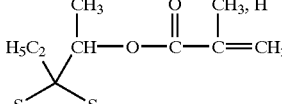
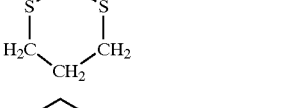
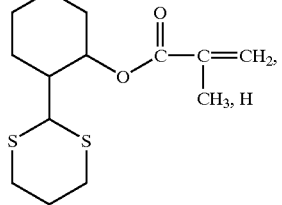

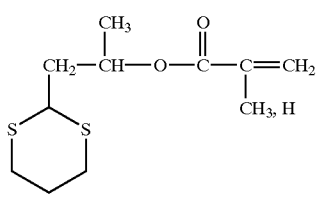
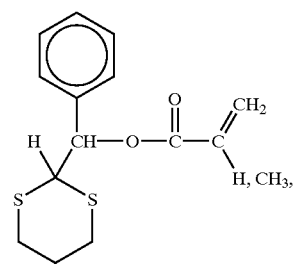
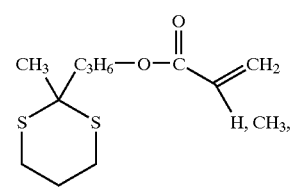
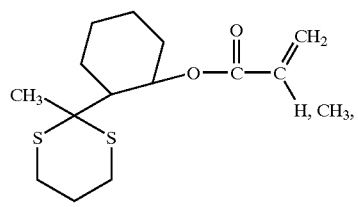
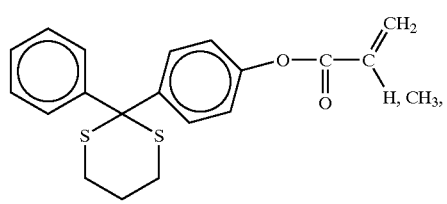
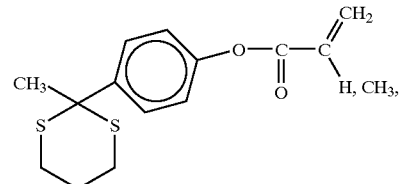
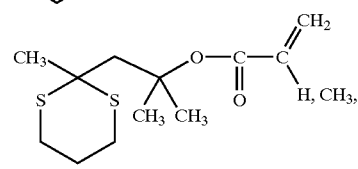
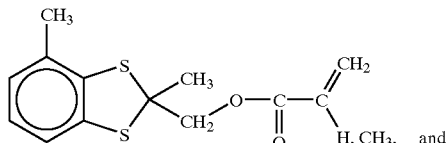
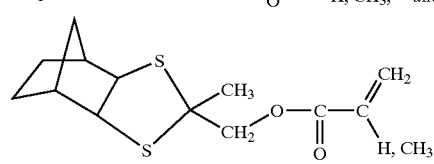
Among the di(meth)acrylic monomers which are preferred according to the invention, mention may be made of the monomers of formulae:
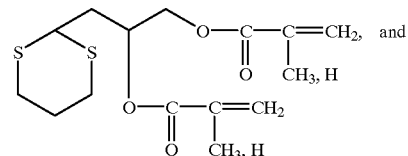
in particular the dimethacrylate.
The remainder of the description gives various examples of the synthesis of the monomers according to the invention.
I. Synthesis of sulfur-containing rings by Dieckmann reaction
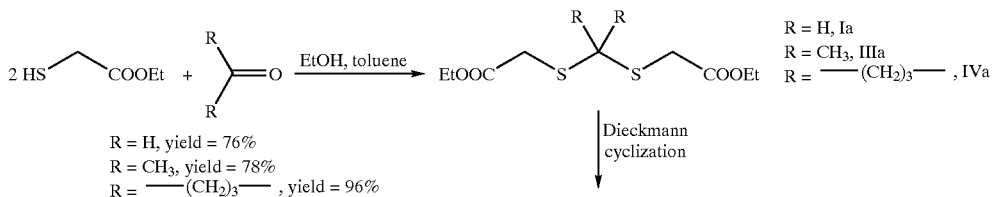
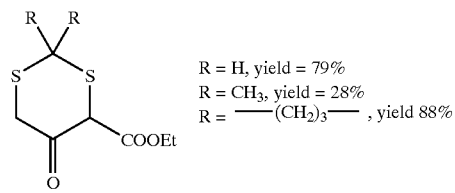

-continued

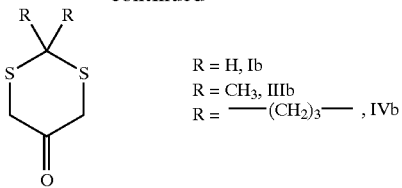

R = H, Ib
R = CH$_3$, IIIb
R = —(CH$_2$)$_3$—, IVb

LiAlH$_4$, THF
R = H, yield = 53%
R = CH$_3$, yield = 54%
R = —(CH$_2$)$_3$—, yield = 78%

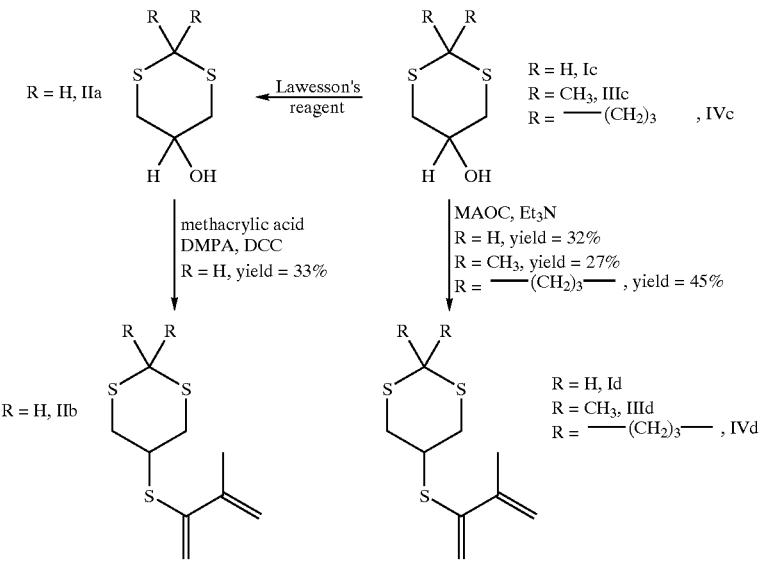

R = H, IIa

Lawesson's reagent

R = H, Ic
R = CH$_3$, IIIc
R = —(CH$_2$)$_3$—, IVc methacrylic acid
DMPA, DCC
R = H, yield = 33%

MAOC, Et$_3$N
R = H, yield = 32%
R = CH$_3$, yield = 27%
R = —(CH$_2$)$_3$—, yield = 45%

R = H, IIb

R = H, Id
R = CH$_3$, IIId
R = —(CH$_2$)$_3$—, IVd

MAOC = methacryloyl chloride
DMAP = dimethylaminopyridine
DCC = dicyclohexylcarbodiimide

I.1 Synthesis of the Diesters Ia, IIIa and IVa 0.2 mol of ethyl mercaptoacetate (2 eq) in 30 ml of toluene and 1 ml of concentrated sulphuric acid is introduced into a 250 ml three-necked flask equipped with a condenser.

The reaction mixture is brought to a temperature of 80° C., followed by dropwise addition of either 0.1 mol of formaldehyde as a 36% solution in water (stabilized with methanol) in the case of the preparation of compound Ia, or 0.1 mol of acetone or cyclohexanone in the case of compounds IIIa and IVa.

After this addition, the reaction mixture is maintained at 100° C. for 2 hours. Stirring is then continued overnight at room temperature.

The reaction mixture is concentrated under reduced pressure. The residue is taken up in dichloromethane and washed successively with 5% sodium hydroxide solution and then with water.

The organic phase is dried over sodium sulphate, filtered and then concentrated under reduced pressure.

The product thus obtained is purified by distillation under reduced pressure.

Ia: diethyl-3,5-dithiaheptane 1,7-dicarboxylate

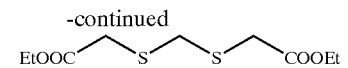

Yield=76%. Boiling point=126° C./0.1 mmHg.

IIIa: diethyl-3,5-dithia(4-dimethyl)heptane 1,7-dicarboxylate

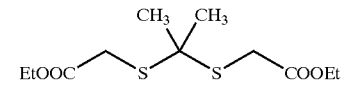

Yield=78% Boiling point=131° C./0.1 mmHg.

IVa: diethyl-3,5-dithia (4-cyclohexyl) heptane 1,7-dicarboxylate

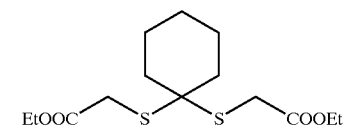

Yield=96% Boiling point=165° C./0.3 mmHg.

I.2 Dieckmann Cyclization: Use of Sodium Methoxide in Ether 0.1 mol (2 eq) of freshly prepared sodium methoxide is suspended in 70 ml of anhydrous ether; 0.05 mol (1 eq) of diester dissolved in 20 ml of anhydrous ether is added dropwise at room temperature. The reaction mixture is then stirred for ten hours at reflux. The reaction mixture is allowed to cool to room temperature and is then poured into a water-ice-acetic acid mixture.

The aqueous phase is extracted with twice 60 ml of ether. The ether phases are washed with dilute sodium hydrogen carbonate solution and then with water.

The organic phase is dried over sodium sulphate and concentrated under reduced pressure.

The β-keto esters thus obtained are used crude in the remainder of the synthesis.

I.3 Decarboxylation of β-keto Esters in Hydrochloric Acid Medium 0.05 mol of β-keto ester and 120 ml of 1N hydrochloric acid solution are introduced into a round-bottomed flask equipped with a condenser. The reaction mixture is maintained at 100° C. for a minimum of 20 hours. The reaction mixture is taken up in 100 ml of ethyl acetate. The aqueous phase is neutralized with sodium hydroxide solution to pH 5.

The organic phase is then washed successively with water and then with saturated sodium chloride solution.

The organic phase is dried over sodium sulphate and then concentrated under reduced pressure.

The thiacycloalcan-3-ones thus obtained will be purified by chromatography on silica gel.

Ib: 1,3-dithiacyclohexan-5-one

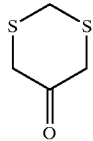

Yield=79% relates to the preceding two steps. Melting point=101° C.

IIIb: 2-dimethyl-1,3-dithiacyclohexan-5-one

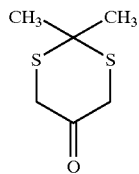

Yield=28% relates to the preceding two steps. Purification eluent: 9% ethyl acetate/91% petroleum ether.

IVb: 2-cyclohexyl-1,3-dithiacyclohexan-5-one

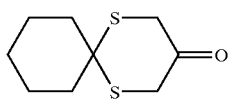

Yield=88% relates to the preceding two steps. Purification eluent: 10% ethyl acetate/90% petroleum ether.

I.4 Reduction of a Ketone with LiAlH$_4$ in THF 0.05 mol (1 eq) of lithium aluminium hydride suspended in 20 ml of anhydrous tetrahydrofuran is introduced, under a nitrogen atmosphere, into a three-necked flask fitted with a condenser, a stirrer and a dropping funnel.

0.05 mol (1 eq) of the ketone obtained in step I.3, dissolved in 10 ml of tetrahydrofuran, is then added dropwise at room temperature.

After addition, the reaction mixture is refluxed for 12 hours. The solution is then allowed to cool to room temperature. The reaction mixture is cooled to 0° C. in order to be hydrolysed with 20 ml of water.

The solution is then poured into 60 ml of 10% sulphuric acid solution. The organic phase is separated out and the aqueous phase is extracted with three times 60 ml of ether. The combined ether phases are washed successively with 50 ml of water and 50 ml of saturated sodium hydrogen carbonate solution and then dried over sodium sulphate and concentrated under reduced pressure.

Ic: 1,3-dithiacyclohexan-5-ol

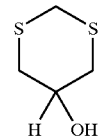

Yield=53%. Purification eluent: 20% ethyl acetate/80% petroleum ether.

IIIc: 2-dimethyl-1,3-dithiacyclohexan-5-ol

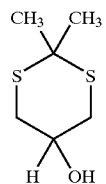

Yield=54%. Purification eluent: % ethyl acetate/% petroleum ether.

IVc: 2-cyclohexyl-1,3-dithiacyclohexan-5-ol

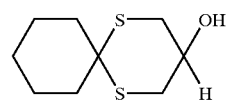

Yield=78%. Purification eluent: % ethyl acetate/% petroleum ether.

I.5 Synthesis of Mercaptans from Alcohols: Use of Lawesson's Reagent 20 mmol (1 eq) of alcohol obtained in the above step, dissolved in 60 ml of toluene, and 11 mmol (0.55 eq) of Lawesson's reagent are introduced under a nitrogen atmosphere.

The reaction mixture is maintained at reflux for a variable period depending on the substrate.

The reaction is monitored by thin layer chromatography.

After the alcohol has disappeared, the reaction mixture is taken up in 100 ml of water and extracted with twice 50 ml of dichloromethane.

The combined organic phases are dried over sodium sulphate and then concentrated under reduced pressure.

The mercaptans thus obtained are used crude in the remainder of the synthesis.

IIa: 1,3-dithiacyclohexan-5-thiol

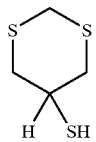

I.6 Coupling of the MAOC with an Alcohol 0.05 mol (1 eq) of alcohol obtained in step I.4, 0.05 mol (1 eq) of triethylamine and 800 ppm of hydroquinone monomethyl ether (HQME) in 300 ml of chloroform are introduced into a three-necked flask fitted with a condenser, a thermometer and a magnetic stirrer. The reaction mixture is cooled to 0° C.; 0.055 mol (1 eq) of methacryloyl chloride dissolved in 20 ml of chloroform is then added dropwise, while maintaining the temperature at 0° C.

After warming to room temperature, the mixture is left stirring for 48 hours.

The reaction mixture is acidified with 50 ml of 6N sulphuric acid solution and is extracted with ether. The organic phase is washed successively with 10% sodium hydrogen carbonate solution and then with saturated sodium chloride solution.

The ether phase is dried over sodium sulphate and the solvent is evaporated off.

The methacrylic compounds thus obtained are purified by chromatography on silica gel.

Id

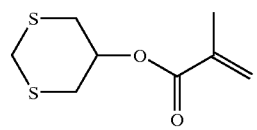

Yield 32%. Purification eluent: 1% ethyl acrylate/99% petroleum ether.

IIId

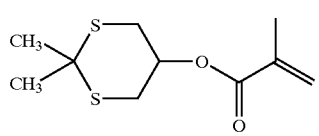

Yield=27%. Purification eluent: 2% ethyl acetate/98% petroleum ether.

IVd

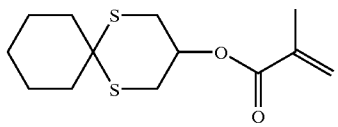

Yield=45%. Purification eluent: 1% ethyl acetate/99% petroleum ether.

I.7 Production of Methacrylic Thioester by Reaction of a Mercaptan with Methacrylic Acid in the Presence of Dicyclohexylcarbodiimide and Dimethylaminopyridine 65 mmol of methacrylic acid and 800 ppm of HQME in 70 ml of dichloromethane are introduced, with stirring, into a 250 ml three-necked flask. 32.5 Mmol of mercaptan obtained in step I.5 and 650 mg of dimethylaminopyridine (DMAP) (catalytic amount of 5% by mass relative to the acid) are added dropwise, at room temperature. The reaction mixture is then cooled to 0° C. and 65 mmol of dicyclohexylcarbodiimide (DCC) are added. Stirring is continued at 0° C. for five minutes and then at room temperature for five hours.

The reaction mixture is filtered in order to remove the dicyclohexylurea formed.

The filtrate is taken up in dichloromethane and the organic phase is washed successively with 0.5 N hydrochloric acid solution and then with 0.5 N sodium hydroxide solution. The organic phase is dried, filtered and concentrated under reduced pressure.

The methacrylic thioester thus obtained is purified by chromatography on silica gel.

IIb

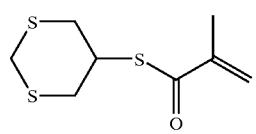

Yield=33%. Purification eluent: 2% ethyl acetate/98% petroleum ether.

II. Preparation of Sulphur-containing Rings by Intermolecular Cyclization Reaction This cyclization method makes it possible to obtain a series of dithiacycloalkane methacrylic monomers according to the scheme below.

The various steps in this synthesis are:

coupling of a dimercaptan with dichloroacetone,
reduction with lithium aluminium hydride in tetrahydrofuran, and
coupling of methacryloyl chloride with the alcohol obtained above.

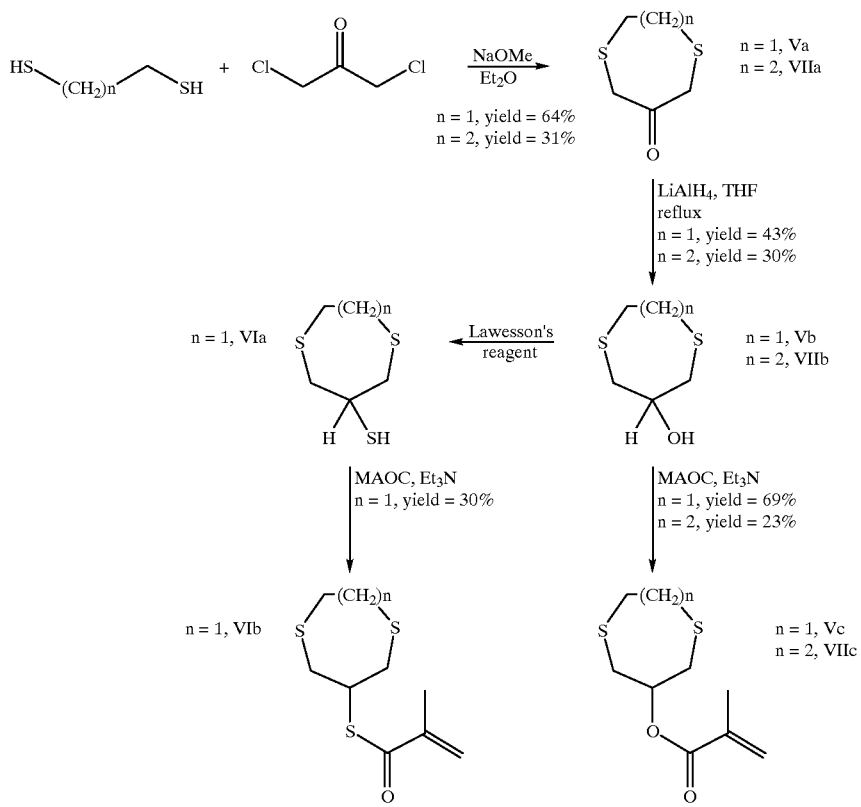

PROCEDURES

II.1 Coupling of Dichloroacetone with a Dimercaptan 0.1 mol (2 eq) of freshly prepared sodium methoxide is dissolved in 20 ml of anhydrous methanol with stirring, followed by addition of 0.05 mol (1 eq) of the dimercaptan at room temperature.

In parallel, a solution of 0.05 mol (1 eq) of 1,3-dichloroacetone dissolved in about 25 ml of anhydrous ether is prepared.

These two solutions are simultaneously introduced into a three-necked flask with stirring, at room temperature and under a nitrogen atmosphere, over a period of about four hours.

At the end of the addition, the reaction mixture is poured into a water-ice-ether mixture containing 10 ml of 10% sodium hydroxide solution.

The aqueous phase is extracted with three times 40 ml of ether. The white precipitate of polymer is separated out by settling. The organic phases are combined, dried over sodium sulphate and concentrated under reduced pressure.

Va: 1,4-dithiacycloheptan-6-one

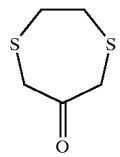

Yield=64%. Purification eluent: 5% ethyl acetate/95% petroleum ether.

VIIa: 1,5-dithiacyclooctan-7-one

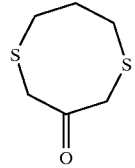

Yield=31%. Purification eluent: 5% ethyl acetate/95% petroleum ether.

II.2 Reduction with LiAlH$_4$ in THF

The procedure is the same as that for step I.4 above.

Vb: 1,4-dithiacycloheptan-6-ol

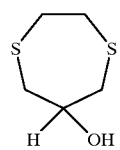

Yield=43%. m.p.=65° C. Purification eluent: 15% ethyl acetate/85% petroleum ether.

VIIb: 1,5-dithiacyclooctan-7-ol

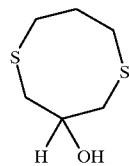

Yield=30%. Purification eluent: 10% ethyl acetate/90% petroleum ether.

II.3 Synthesis of Mercaptans from Alcohols: Use of Lawesson's Reagent

The procedure is the same as that in step I.5 above.

VIa: 1,4-dithiacycloheptan-6-thiol

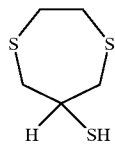

II.4 Coupling of MAOC with an Alcohol

The procedure is the same as that in step I.6 above.

Vc

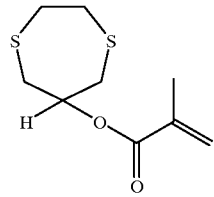

Yield=69%. Purification eluent: 5% ethyl acetate/95% petroleum ether.

VIIc

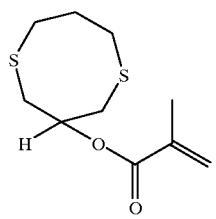

Yield=23%. Purification eluent: 2% ethyl acetate/98% petroleum ether.

II.5 Reaction of MAOC with a Mercaptan in the Presence of a Tertiary Base 55 mmol of MAOC diluted in 25 ml of solvent (acetonitrile, acetone or toluene) to which 800 ppm of HQME have been added are introduced into a reactor under a nitrogen atmosphere, fitted with a thermometer and a dropping funnel. The reaction mixture is cooled to −10° C. and the mixture: mercaptan from step II.3 (50 mmol)/triethylamine (55 mmol) diluted in 10 ml of solvent, is added dropwise.

Stirring is continued at the same temperature for five hours.

After filtering off the salt formed, the solvent is removed. The residue is taken up in dichloromethane and washed with 0.5 N sodium hydroxide solution; the organic phase is dried over sodium sulphate and concentrated under reduced pressure.

The methacrylic thioesters thus obtained are purified by chromatography on silica gel.

VIb

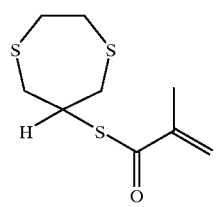

Yield=30%. Purification eluent: 1% ethyl acetate/99% petroleum ether.

III. Preparation of Sulphur-containing Rings Containing the S-S Unit

The various steps in this synthesis are:

treatment of a dihalo derivative with sodium disulphide ($Na_2S_2$) which allows the cyclic disulphide to be obtained. This method uses a phase transfer catalysis reaction;

next, coupling of methacryloyl chloride with the alcohol obtained above.

$$Br\diagdown(CH_2)_n\diagup Br \;+\; Na_2S, 9H_2O \;+$$

$$n = 1,2$$

$$S(NaOH\;aq.) \xrightarrow{NBu_4^\oplus, HSO_4^\ominus}{CH_3Cl_2}$$

n = 1, yield = 76%
n = 2, yield = 95%

$$\underset{OH}{\underset{|}{\overset{S-S}{\diagup\diagdown}}(CH_2)_n}\quad\begin{array}{l}n = 1, VIIIa\\ n = 2, IXa\end{array}$$

$$\Big\downarrow\begin{array}{l}MAOC,\;Et_3N\\ n = 1,\;yield = 56\%\\ n = 2,\;yield = 51\%\end{array}$$

n = 1, VIIIb
n = 2, IXb

PROCEDURES

III.1 Preparation of the Alcohols VIIIa and IXa

¼ mol of $Na_2S.9H_2O$ is dissolved in 100 ml of water in a three-necked flask fitted with a thermometer and a condenser, and this solution is brought to 40° C. 3 sodium hydroxide pellets are then added, followed by sulphur, so as to obtain the desired Na$_2$S$_2$ system (8 g, ¼ mol for n=2).

The mixture is cooled to room temperature and ¼ mol of dibromo derivative in 100 ml of dichloromethane is then added. Tetrabutylammonium hydrogen sulphate (phase transfer catalyst) is then added (5 mol % relative to the halo derivative).

This solution is refluxed for one hour with stirring and is then cooled to room temperature over one hour. The organic phase is taken up in dichloromethane and then washed with water and finally dried over sodium sulphate. The solvent is then evaporated off under reduced pressure. The ring thus obtained is purified by chromatography on silica gel.

VIIIa: 1,2-dithiacyclopentan-4-ol

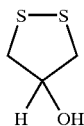

Yield=77%. Purification eluent: 20% ethyl acetate/80% petroleum ether.

IXa: 1,2-dithiacylcohexan-4-ol

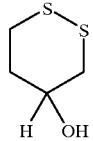

Yield=95%. Purification eluent: 20% ethyl acetate/80% petroleum ether.

III.3 Addition reaction of MAOC with an alcohol
The procedure is the same as that in step I.6 above.

VIIIb

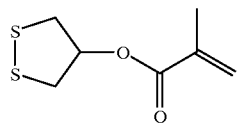

Yield=56%. Purification eluent: 2% ethyl acetate/98% petroleum ether.

IXb

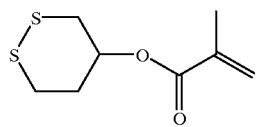

Yield=50%. Purification eluent: 2% ethyl acetate/98% petroleum

IV. Synthesis of a trithiane-derived methacrylic monomer

-continued

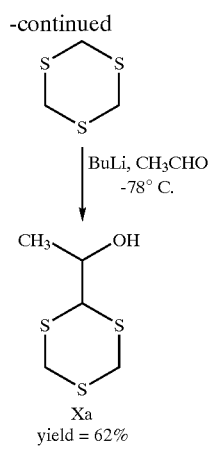

Xa
yield = 62%

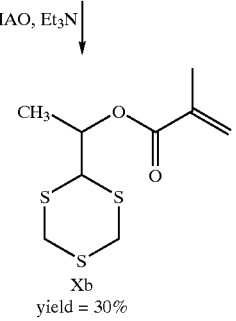

Xb
yield = 30%

PROCEDURES

IV.1 Addition Reaction of an Electrophile to Trithiane 5 g (36 mmol) of trithiane dissolved in 70 ml of anhydrous tetrahydrofuran are introduced into a three-necked flask under a nitrogen atmosphere. The reaction mixture is cooled to −30° C., at which temperature 1.05 eq of nBuLi (1.6M as a solution in hexane) are added slowly. This step is exothermic and the reaction mixture turns yellow.

The temperature is maintained between −25 and −15° C. for two hours thirty minutes. After this period, the trithiane should be entirely dissolved. Lastly, the reaction mixture is cooled to −70° C. and the aldehyde dissolved in tetrahydrofuran is then added dropwise by syringe. The reaction mixture is stirred overnight at a temperature of between 0 and 25° C.

Stirring is continued for a further one hour at room temperature and the reaction mixture is poured into an H$_2$O/CCl$_4$ mixture. The aqueous phase is extracted three times with carbon tetrachloride. The organic phases are collected and the trithiane in suspension is filtered off. The organic phase is washed three times with water and then dried, filtered and concentrated under reduced pressure.

Xa

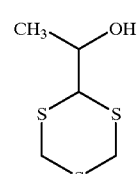

Yield=62%.

IV.2 Coupling of MAOC with the Trithiane Alcohol

The procedure is the same as that in step I.6 above.

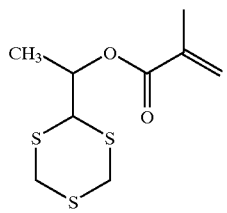
Xb

Yield=30%. Purification eluent: 2% ethyl acetate/98% petroleum ether.

V. Synthesis of Dithiane-derived Methacrylic Monomers

First synthetic scheme

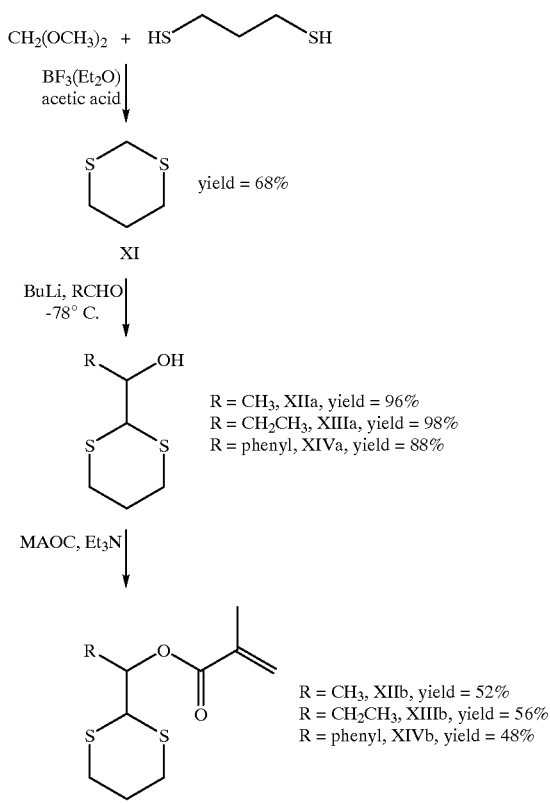

Second synthetic scheme

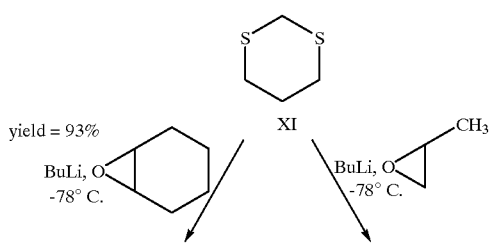

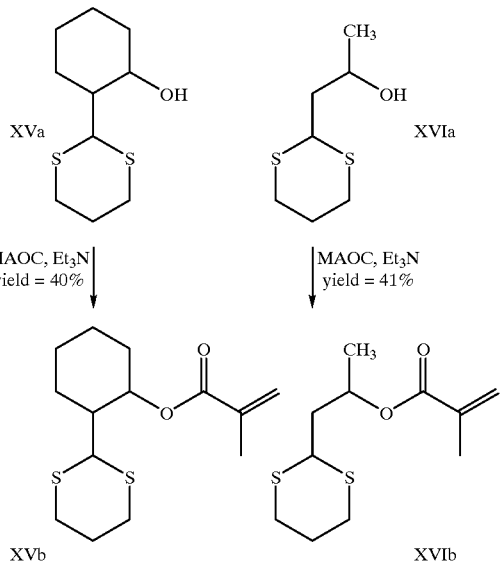

PROCEDURES

V.1 Synthesis of Dithiane 36 ml of $BF_3$ etherate and 72 ml of glacial acetic acid in 120 ml of chloroform are introduced into a three-necked flask fitted with a condenser, a magnetic stirrer and a dropping funnel. The reaction mixture is brought to reflux and the mixture: 30 ml (0.3 mol) of propanedithiol, 29 ml of dimethoxymethane (0.33 mol) dissolved in 450 ml of chloroform, is then added dropwise. The addition is carried out slowly over a period of eight hours. The reaction mixture is allowed to return to room temperature and is then washed successively with four times 80 ml of water, twice 120 ml of 10% potassium hydroxide solution and again with twice 80 ml of water. The organic phase is dried over sodium sulphate and filtered and the solvent is then evaporated off under reduced pressure.

The solid residue is taken up in 60 ml of methanol and heated to the boiling point of the methanol. A hot filtration is carried out, the filtrate is allowed to return to room temperature and this solution is finally kept at −20° C. overnight. The white crystals of dithiane are collected by filtration and dried.

XI: 1,3-dithiane

Yield=68%. Melting point=55° C.

V.2 Addition Reaction of an Electrophile to 1,3-Dithiane 5 g (41.6 mmol) of dithiane dissolved in 80 ml of anhydrous tetrahydrofuran are introduced into a three-necked flask under a nitrogen atmosphere.

The reaction mixture is cooled to −40° C., at which temperature 27.3 ml (43.68 mmol, 1.05 eq) of nBuLi (1.6 M as a solution in hexane) are added dropwise. The reaction medium is then stirred for two hours at a temperature of between −20 and −40° C. After this period, the mixture is cooled to −70° C. and the electrophile (aldehyde or epoxide) dissolved in the minimum amount of tetrahydrofuran is added slowly.

In the case of an aldehyde, the reaction is instantaneous. In the case of an epoxide, the reaction is monitored by thin layer chromatography.

Once the reaction is complete, the reaction mixture is hydrolysed slowly under cold conditions with water.

The aqueous phase is extracted three times with ether.

The organic phases are combined, washed three times with water and then with saturated sodium chloride solution.

The organic phases are dried over sodium sulphate and the solvent is then evaporated off under reduced pressure.

The product thus obtained is purified by chromatography on silica gel.

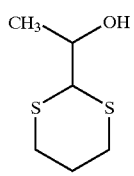

XIIa

Electrophile: acetaldehyde

Yield=96%. Purification eluent: 10% ethyl acetate/90% petroleum ether.

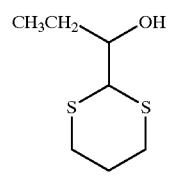

XIIIa

Electrophile: propionaldehyde

Yield=98%. Purification eluent: 10% ethyl acetate/90% petroleum ether.

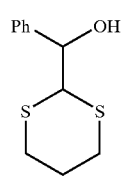

XIVa

Electrophile: propionaldehyde
2-(hydroxyphenylmethyl)-1,3-dithiane

Yield=88%. M.p.=73° C. Purification eluent: 12% ethyl acetate/88% petroleum ether.

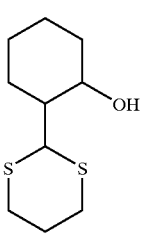

XVa

Electrophile: cyclohexene oxide

Yield=93%. Purification eluent: 10% ethyl acetate/90% petroleum ether.

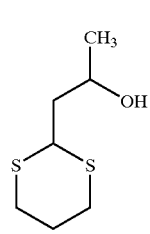

XVIa

Electrophile: propylene oxide

Yield=72%. Purification eluent: 11% ethyl acetate/89% petroleum ether.

V.3 Coupling of MAOC with the Alcohol

The procedure is the same as that in step I.6 above.

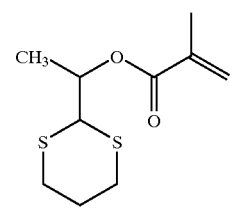

XIIb

Yield=52%. Purification eluent: 2% ethyl acetate/98% petroleum ether.

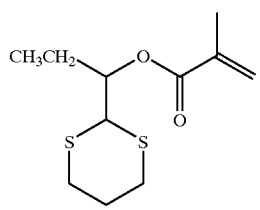

XIIIb

Yield=56%. Purification eluent: 3% ethyl acetate/97% petroleum ether.

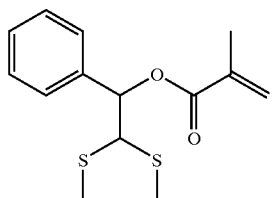

XIVb

2-[α-(2-propenylcarbonyloxy)benzyl]-1,3-dithiane

Yield=48%. M.p.=97° C. Purification eluent: 5% ethyl acetate/95% petroleum ether.

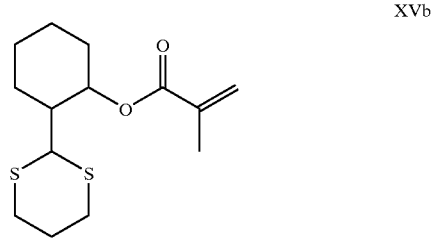 XVb

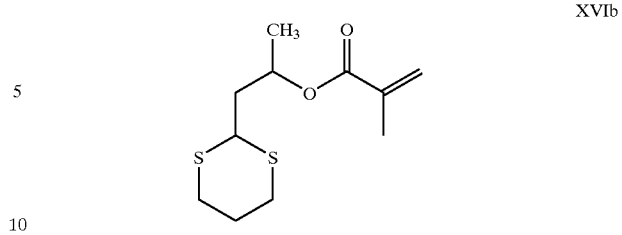 XVIb

Yield=40%. Purification eluent: 2% ethyl acetate/98% petroleum ether.

Yield=41%. Purification eluent: 3% ethyl acetate/97% petroleum ether.

VI. Synthesis of alkyldithiane-derived methacrylic monomers

<u>1st synthetic route</u>

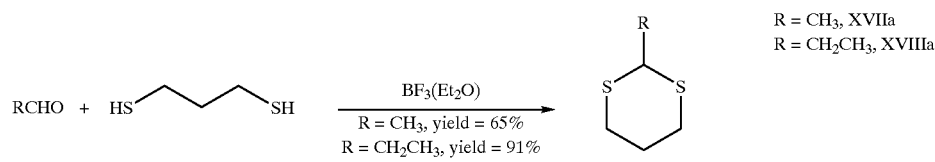

R = CH$_3$, XVIIa
R = CH$_2$CH$_3$, XVIIIa

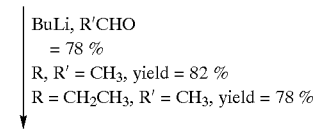

BuLi, R'CHO
= 78 %
R, R' = CH$_3$, yield = 82 %
R = CH$_2$CH$_3$, R' = CH$_3$, yield = 78 %

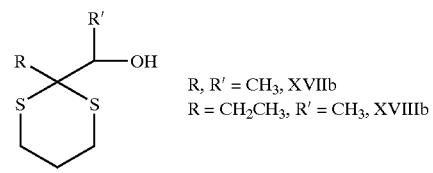

R, R' = CH$_3$, XVIIb
R = CH$_2$CH$_3$, R' = CH$_3$, XVIIIb

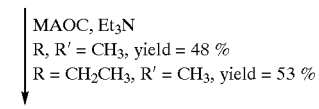

MAOC, Et$_3$N
R, R' = CH$_3$, yield = 48 %
R = CH$_2$CH$_3$, R' = CH$_3$, yield = 53 %

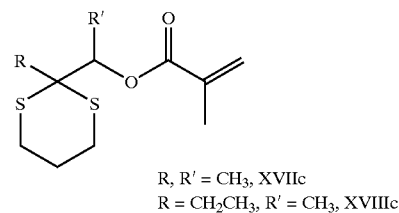

R, R' = CH$_3$, XVIIc
R = CH$_2$CH$_3$, R' = CH$_3$, XVIIIc

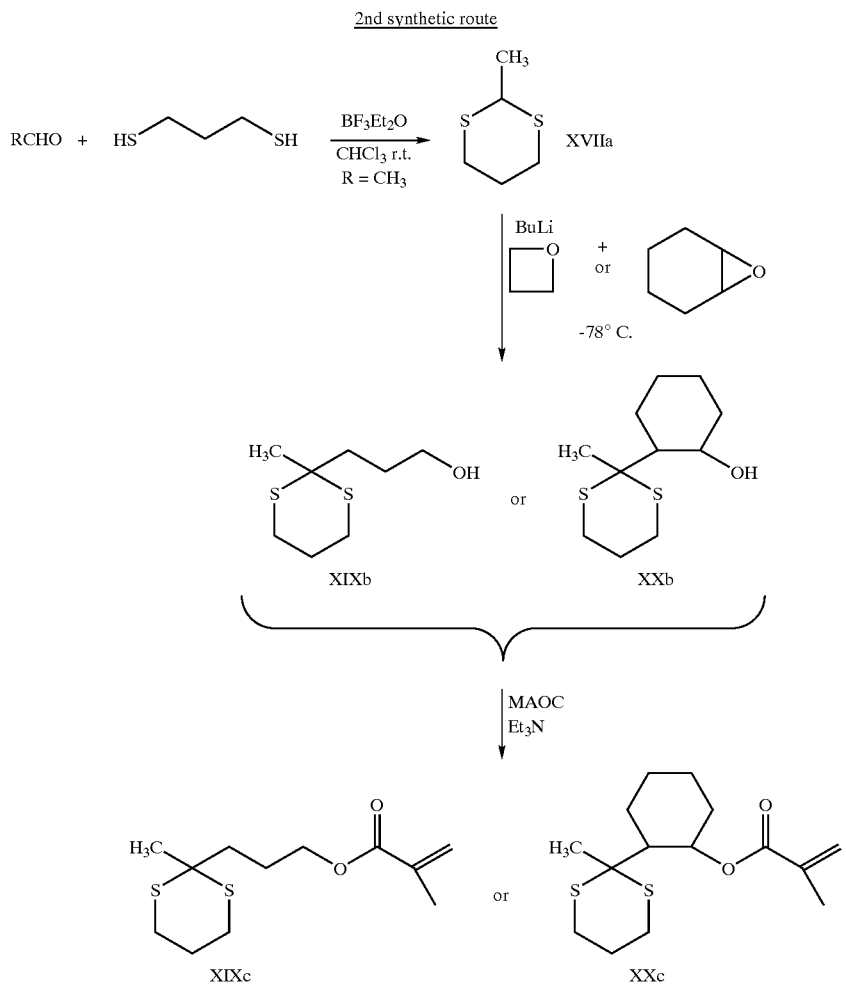

VI.1 Preparation of 2-Methyl-1,3-dithiane and 2-Ethyl-1,3-dithiane 5 g (46.2 mmol) of 1,3-propanedithiol and 46.2 mmol of aldehyde (acetaldehyde or propionaldehyde) in 60 ml of chloroform are introduced into a three-necked flask. This solution is stirred for one hour at a temperature of −20° C. Next, 46.2 mmol of $BF_3$ etherate are added slowly and the mixture is allowed to return to room temperature over fifteen hours.

The reaction mixture is washed three times with water and then with 10% potassium hydroxide solution. The organic phase is dried over sodium sulphate, filtered and then concentrated under reduced pressure.

XVIIa: 2-methyl-1,3-dithiane

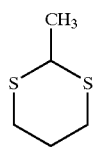

Yield=85%. Purification eluent: 3% ethyl acetate/97% petroleum ether.

XVIIIa: 2-ethyl-1,3-dithiane

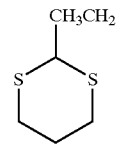

Yield=81%. Purification eluent: 2% ethyl acetate/98% petroleum ether.

VI.2 Addition of an Electrophile to the Alkyldithiane

The procedure is the same as that in step V.2 above.

Electrophile: acethaldehyde

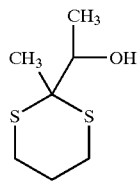
XVIIb

Yield=82%. Purification eluent: 9% ethyl acetate/81% petroleum ether.

Electrophile: acethaldehyde

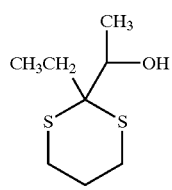
XVIIIb

Yield=78%. Purification eluent: 9% ethyl acetate/91% petroleum ether.

Electrophile: oxetane (trimethylene oxide)

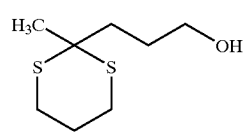
XIXb 2-methyl-2-(3'-hydroxy-1'-propyl)-1,3-dithiane

Yield=71%.

Electrophile: cyclohexene oxide

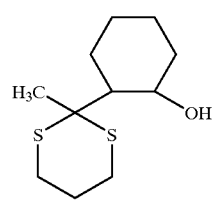
XXb 2-methyl-2-(2'-hydroxy-1'-cyclohexyl)-1,3-dithiane

Yield=89%.

VI.3 Addition of MAOC to an Alcohol

The procedure is the same as that in step I.6 above.

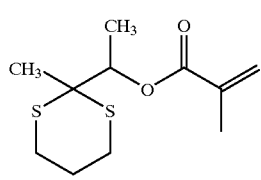
XVIIc

Yield=48%. Purification eluent: 1% ethyl acetate/99% petroleum ether.

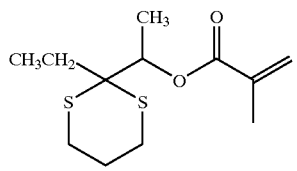
XVIIIc

Yield=53%. Purification eluent: 4% ethyl acetate/96% petroleum ether.

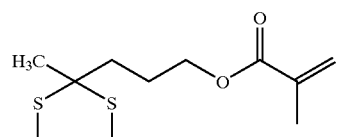
XIXc 2-methyl-2-(2-propenylcarbonyloxytrimethylene)-1,3-dithiane

Yield=71%. $n_D^{20}$=1.5268 $v_D$=39.9 Purification eluent: 5% ethyl acetate/95% petroleum ether.

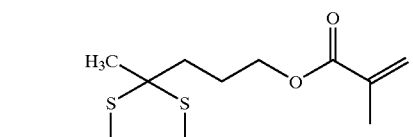
XXc 2-methyl-2-[2-(2-propenylcarbonyloxy)cyclohexyl]-1,3-dithiane

Yield=14%. $n_D^{20}$=1.5425 $v_D$=41.7 Purification eluent: 4% ethyl acetate/96% petroleum ether.

The optical properties of the monomers synthesized above were evaluated by measuring their refractive index and their Abbe number. The various results are indicated in Table I below.

TABLE I

| Product structural formula | Product number | $n_D^{20}$ | $v_D$ |
|---|---|---|---|
| 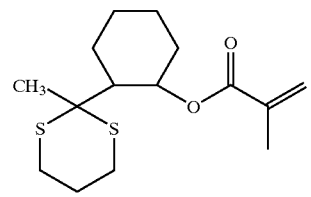 | Id | 1.5509 | 37.0 |
|  | IIb | 1.5960 | 31.6 |
|  | IIId | 1.5215 |  |

TABLE I-continued

| Product structural formula | Product number | $n_D^{20}$ | $v_D$ |
|---|---|---|---|
| (cyclohexane spiro dithiane methacrylate) | IVd | 1.5462 | 40.1 |
| (dithiepane methacrylate) | Vc | 1.5447 | 39.5 |
| (dithiepane thiomethacrylate) | VIb | 1.5923 | 33.9 |
| (dithiocane methacrylate) | VIIc | 1.5393 | 38.8 |
| (dithiolane methacrylate) | VIIIb | 1.5163 | 38.0 |
| (dithiane methacrylate) | IXb | 1.5419 | 36.0 |
| (trithiane ethyl methacrylate) | Xb | 1.5690 | 36.9 |
| (dithiane ethyl methacrylate) | XIIb | 1.5330 | 44.2 |
| (dithiane propyl methacrylate) | XIIIb | 1.5202 | 39.5 |

TABLE I-continued

| Product structural formula | Product number | $n_D^{20}$ | $v_D$ |
|---|---|---|---|
| (cyclohexyl dithiane methacrylate) | XVb | 1.5288 | 40.2 |
| (dithiane methyl methacrylate) | XVIb | 1.5280 | 40.0 |
| (dimethyl dithiane methacrylate) | XVIIc | 1.5300 | 39.2 |
| (ethyl methyl dithiane methacrylate) | XVIIIc | 1.5273 | 40.5 |
| (methyl dithiane propyl methacrylate) | XIXc | 1.5268 | 39.9 |
| (cyclohexyl methyl dithiane methacrylate) | XXc | 1.5425 | 41.7 |

Summary scheme

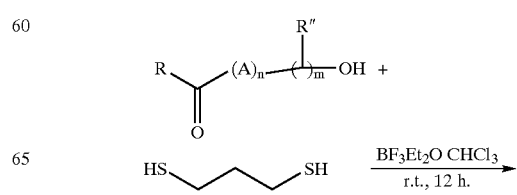

-continued

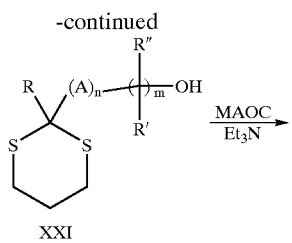

XXI

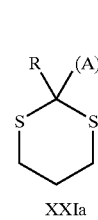

XXIa

A=CH$_2$, Ph
n=0, 1
R', R", R=H, CH$_3$, Ph

VII-1 Synthesis of Cyclic 1,3-Dithioacetals by Addition Reaction of a Dimercaptan to a Ketone 46.2 mmol of propanedithiol and 46.2 mmol of hydroxy ketone in 60 ml of chloroform are introduced into a three-necked flask. This solution is stirred for 1 hour at a temperature of −20° C. Next, 46.2 mmol of boron trifluoride etherate are added slowly and the mixture is allowed to return to room temperature over 12 hours.

The reaction mixture is washed three times with water and then with 10% potassium hydroxide solution. The organic phase is dried over sodium sulphate, filtered and then concentrated under reduced pressure. In the case of hydroxyphenyl ketones, the organic phase does not undergo any basic washing. The products thus obtained are purified by chromatography on silica gel.

(XXII)

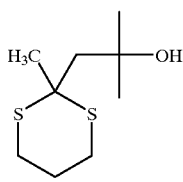

Yield=98%.

XXIII

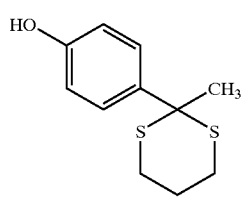

2-methyl-2-(4'-hydroxy-1'-phenyl)-1,3-dithiane

Yield=98%.

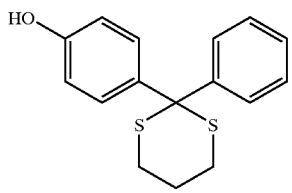

XXIV 2-phenyl-2-(4'-hydroxy-1'-phenyl)-1,3-dithiane

Yield=95%.

VII-2 Synthesis of Methacrylic Esters by Coupling Methacryloyl Chloride with an Alcohol 50 mmol (1 eq) of alcohol, 50 mmol (1 eq) of triethylamine and 800 ppm of HQME in 30 ml of chloroform are introduced into a three-necked flask fitted with a condenser, a thermometer and a magnetic stirrer. The reaction mixture is cooled to 0° C.; next, 55 mmol (1.1 eq) of methacryloyl chloride dissolved in 20 ml of chloroform are added dropwise, while maintaining the temperature at 0° C. After returning to room temperature, the mixture is left stirring for 48 hours.

The reaction mixture is acidified with 50 ml of 6N sulphuric acid solution and extracted with ether. The organic phase is washed successively with 10% sodium hydrogen carbonate solution and then with saturated sodium chloride solution. The ether phase is dried over sodium sulphate and the solvent is evaporated off. The methacrylic compounds thus obtained are purified by chromatography on silica gel.

XXIIa

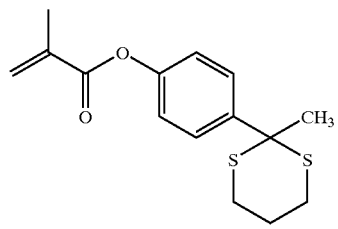

2-methane-2-[2-methyl-2-(2-propenylcarbonyloxy)propyl]-1,3-dithiane

Yield=32%. $n_D^{20}$=1.5215 $v_D$=38.6 Purification eluent: 1% ethyl acetate/99% petroleum ether.

XXIIIa 2-methyl-2-[4-(2-propenecarbonyloxy)phenyl]-1,3-dithiane

Yield=50%. $n_D^{20}$=1.5742 $v_D$=30.8 Purification eluent: 4% ethyl acetate/96% petroleum ether.

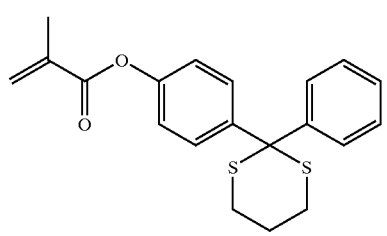

2-phenyl-2-[4-(2-propenylcarbonyloxy)phenyl]-1,3-dithiane

Yield=48%. m.p.=132° C. Purification eluent: 2% ethyl acetate/98% petroleum ether.

VIII—Synthesis of 2-Methyl-2-(2-propenylcarbonyl-oxymethyl)-5-methyl-1,3-benzodithiolane and 4-Methyl-4-(2-propenylcarbonyloxymethyl)-3,5-dithia-tricyclo[5,2,1,0$^{(2,6)}$]Decane Synthetic scheme

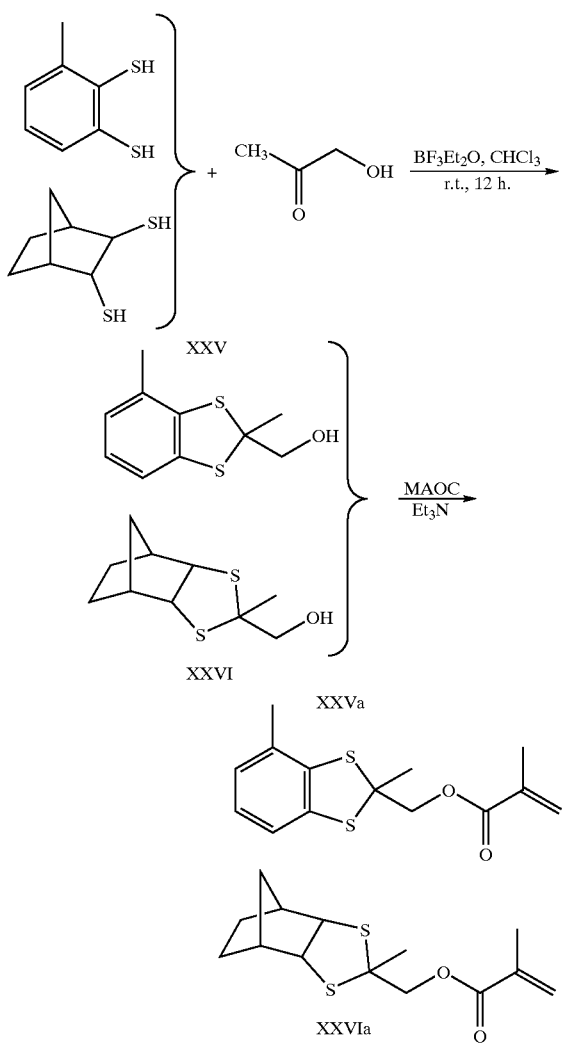

VIII—1 Synthesis of the Alcohols 46.2 mmol of dimercaptan and 46.2 mmol of hydroxyacetone in 60 ml of chloroform are introduced into a three-necked flask. This solution is stirred for 1 hour at a temperature of −20° C. Next, 46.2 mmol of boron trifluoride etherate are added slowly and the mixture is allowed to return to room temperature over 12 hours.

The reaction mixture is washed three times with water and then with 10% potassium hydroxide solution. The organic phase is dried over sodium sulphate, filtered and then concentrated under reduced pressure. The products thus obtained are purified by chromatography on silica gel.

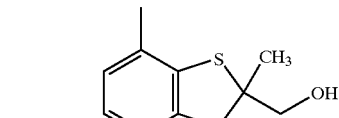

2-methyl-2-hydroxymethyl-5-methyl-1,3-benzodithiolane

Yield=quantitative. Purification eluent: 10% ethyl acetate/ 90% petroleum ether.

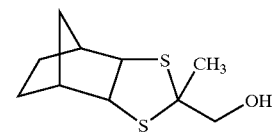

4-methyl-4-hydroxymethyl-3,5-dithiatricyclo[5,2,1,0$^{(2,6)}$]decane

Yield=67%.

VIII—2 Synthesis of Methacrylic Esters by Coupling Methacryloyl Chloride with an Alcohol 50 mmol (1 eq) of alcohol, 50 mmol (1 eq) of triethylamine and 800 ppm of HQME in 30 ml of chloroform are introduced into a three-necked flask fitted with a condenser, a thermometer and a magnetic stirrer. The reaction mixture is cooled to 0° C.; next, 55 mmol (1 eq) of methacryloyl chloride dissolved in 20 ml of chloroform are added dropwise, while maintaining the temperature at 0° C. After returning to room temperature, the mixture is left stirring for 48 hours.

The reaction mixture is acidified with 50 ml of 6N sulphuric acid solution and is extracted with ether. The organic phase is washed successively with 10% sodium hydrogen carbonate solution and then with saturated sodium chloride solution. The ether phase is dried over sodium sulphate and the solvent is evaporated off. The methacrylic compounds thus obtained are purified by chromatography on silica gel.

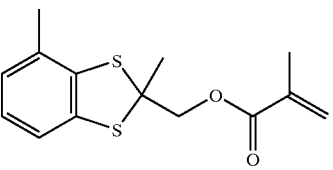

2-methyl-2-(2-propenylcarbonyloxymethyl)-5-methyl-1,3-benzodithiolane

Yield=38%. $n_D^{20}$=1.5706 $v_D$=27.5 Purification eluent: 1% ethyl acetate/99% petroleum ether.

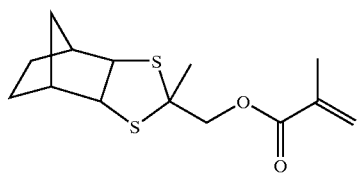

4-methyl-4-(2-propenylcarbonyloxymethyl)-3,5-dithiatricyclo[5,2,1,0$^{(2,6)}$]decane Yield=30%. $n_D^{20}$=1.5294 $v_D$=37.6 Purification eluent: 1% ethyl acetate/99% petroleum ether.

IX—Synthesis of 2-[2,2-bis(2-Propenylcarbonyloxy)-propyl]-1,3-dithiane

Synthetic scheme

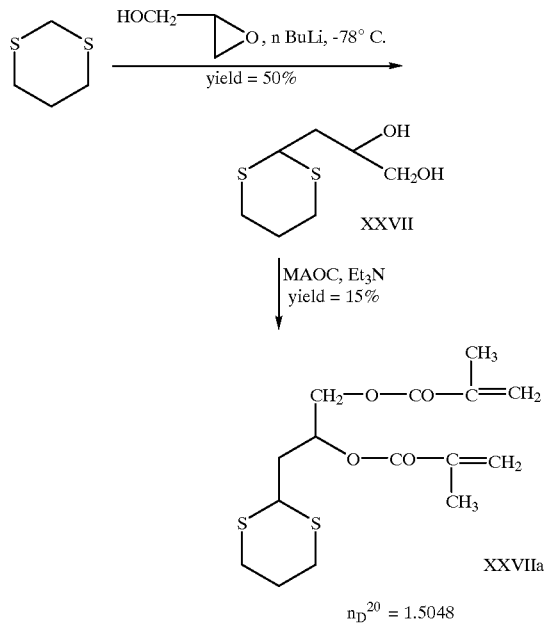

$n_D^{20}$ = 1.5048

Procedure

The procedure is similar to that described above in V.2 and I.6.

The structures of the monomers were confirmed by NMR spectrography.

The $^1$H NMR spectra were recorded at 250 MHz on a Bruker AC 250 machine. The proton-decoupled $^{13}$C NMR spectra were recorded at 62.88 MHz on a Bruker AC 250 machine. The technique used is Spin Echo Fourier Transform (SEFT).

Tetramethylsilane was used as internal reference.

The thin layer chromatographies were carried out on silica plates (Kieselgel 60F$_{254}$) and developed using potassium permanganate or iodine.

The mass spectra were acquired on a Hewlett-Packard 5971A machine by electron impact (ionization voltage: 70 eV). The spectrometer is coupled to a gas chromatograph (capillary column of WCOT Fused Silica type, stationary phase: CP-Sil CB, length: 25 metes, inside diameter: 0.25 mm, film thickness: 0.12 μm).

The refractive indices $n_D^{20}$ were measured at 20° C. on an Abbe refractometer (ASTM-NFT 60194 model) for the sodium D line (589.3 nm).

The Abbe numbers ($v_D$) were calculated from the refractive index measurements at the following wavelengths: 480 nm (F' of cadmium), 546.1 nm (E of mercury), 589.3 nm (D of sodium), 643.8 nm (C' of cadmium). $v_D$ is deduced by the formula: $v^D$=($n_D$~1)/($n_{F'}$~$n_{C'}$)

The solvents were distilled before use:
anhydrous ether dried over Na$_2$SO$_4$, distilled over sodium and stored over sodium.
anhydrous tetrahydrofuran distilled over sodium in the presence of benzophenone and stored over sodium.
anhydrous acetone dried over CaCl$_2$, distilled over KMnO$_4$, dried over K$_2$CO$_3$ and stored over 4 Å molecular sieves.
anhydrous methylene chloride distilled over P$_2$O$_5$ and stored over 4 Å molecular sieves.
methylene chloride and ether distilled over P$_2$O$_5$.
methanol distilled over magnesium.

The present invention also relates to novel compounds which are useful as intermediates for the synthesis of monomers according to the invention.

More particularly, these novel compounds which are useful as synthetic intermediates are thiol compounds corresponding to the formula:

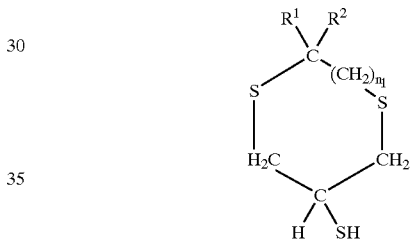

in which R$^1$, R$^2$ and n$_1$ are defined as above. Preferably, R$^1$ and R$^2$ both represent a hydrogen atom.

Among these novel compounds, mention may be made of the compounds of formulae:

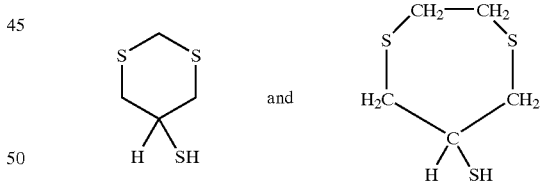

The present invention also relates to polymerizable compositions containing at least one functional monomer of mono(thio)(meth)acrylate or di(meth)acrylate type, preferably mono(thio)(meth)acrylate, bearing a 5- to 8-membered heterocycle consisting of hydrogen, carbon and sulphur atoms and having at least two endocyclic sulphur atoms.

The heterocycle which -is useful in the compositions according to the invention is preferably 6-membered.

Preferably also, the heterocycle of the monomer which is useful in the polymerizable compositions according to the invention contains two endocyclic sulphur atoms in positions 1–3 or 1–4 of the heterocycle.

In another recommended embodiment of the polymerizable compositions according to the invention, the heterocycle of the monomer is a 6-membered heterocycle containing three endocyclic sulphur atoms. Also, the monomers of mono(thio)(meth)acrylate type which are particularly recommended for the polymerizable compositions according to the present invention are thio(meth) acrylate monomers. Lastly, these monomers preferably have a molar mass of between 150 and 350 and better still between 200 and 300.

The monomers of mono(thio)(meth)acrylate type which are particularly recommended in the polymerizable compositions of the present invention are the monomers described above and represented by the formula (A), and most especially those for which, in formula (A), X represents a sulphur atom.

The polymerizable compositions according to the invention can comprise only one functional monomer according to the invention or a mixture thereof, or alternatively the compositions can contain a monomer or a mixture of monomers according to the invention as described above, with one or more other common monomers which can be copolymerized with the monomers of the invention, for the manufacture, by polymerization, of transparent polymers which have suitable optical and/or ophthalmic properties.

Any suitable comonomer which can be copolymerized with the monomers according to the invention can be used in the polymerizable compositions according to the invention.

Among the comonomers which can be used with the monomers of (thio)(meth)acrylate type for the polymerizable compositions according to the invention, mention may be made of mono- or polyfunctional vinyl, acrylic and methacrylic monomers.

Among the vinyl comonomers which are useful in the compositions of the present invention, mention may be made of vinyl alcohols and vinyl esters such as vinyl acetate and vinyl butyrate.

The acrylic and methacrylic comonomers can be mono- or polyfunctional alkyl(meth)acrylate comonomers and polycyclenic or aromatic mono(meth)acrylate comonomers.

Among the alkyl(meth)acrylates, mention may be made of styrene, α-alkylstyrenes such as α-methyl styrene, methyl (meth)acrylate, ethyl(meth)acrylate, butyl(meth)acrylate, isobutyl(meth)acrylate or difunctional derivatives such as butanediol dimethacrylate, or trifunctional derivatives such as trimethylolpropane trimethacrylate.

Among the polycyclenic mono(meth)acrylate comonomers, mention may be made of cyclohexyl (meth) acrylate, methylcyclohexyl(meth)acrylate, isobornyl(meth) acrylate and adamantyl(meth)acrylate.

Comonomers which may also be mentioned are aromatic mono(meth)acrylates such as phenyl (meth)acrylate, benzyl (meth)acrylate, 1-naphthyl (meth)acrylate, fluorophenyl (meth)acrylate, chlorophenyl (meth)acrylate, bromophenyl (meth)acrylate, tribromophenyl(meth)acrylate, methoxyphenyl (meth)acrylate, cyanophenyl(meth)acrylate, biphenyl (meth)acrylate, bromobenzyl(meth)acrylate, tribromobenzyl(meth) acrylate, bromobenzylethoxy(meth) acrylate, tribromobenzylethoxy(meth)acrylate and phenoxyethyl(meth)acrylate.

Among the comonomers which can be used in the compositions according to the invention, mention may also be made of allylcarbonates of linear or branched, aliphatic or aromatic, liquid polyols such as aliphatic glycol bis (allylcarbonates) or alkylenebis(allylcarbonates). Among the polyol(allylcarbonates) which can be used to prepare the transparent polymers which can be used in accordance with the invention, mention may be made of ethylene glycol bis(allylcarbonate), diethylene glycol bis (2-methallylcarbonate), diethylene glycol bis (allylcarbonate), ethylene glycol bis(2-chloroallylcarbonate), triethylene glycol bis(allylcarbonate), 1,3-propanediol bis(allyl-carbonate), propylene glycol bis (2-ethylallyl-carbonate), 1,3-butanediol bis(allylcarbonate), 1,4-butanediol bis(2-bromoallylcarbonate), dipropylene glycol bis(allylcarbonate), trimethylene glycol bis(2-ethylallylcarbonate), pentamethylene glycol bis (allylcarbonate) and isopropylene bisphenol bis (allylcarbonate).

The comonomers which can be used in the compositions according to the invention also comprise cellulose esters such as cellulose acetate, cellulose propionate and cellulose butyrate.

Comonomers which can also be used are monomers of the polyalkylene glycol di(meth)acrylate type or aromatic di(meth)acrylate derivatives such as 2,2-bis-4-methacryloyloxypolyethoxyphenylpropane.

The comonomers which are useful in the present invention also comprise sulphur-containing compounds other than those of formula (A). These can be mono- or poly(meth) acrylates bearing one or more sulphur atoms or alternatively monothio(meth)acrylates or polythio(meth)acrylates, for example such as those described in patent application EP-273,710. Among the polythio(meth)acrylates, mention may be made of bis-2 methacryloylthioethyl sulphide and 4,4'-bis-methacryloylthiophenyl sulphide.

For an additional description of the comonomers which can be used in the compositions according to the invention, reference may be made to French patent No. 2,699,541.

The polymerization of the polymerizable compositions according to the invention can be carried out by any known polymerization process. The polymerization process which is particularly suitable in the present invention is photochemical polymerization. A recommended polymerization process is photochemical polymerization via ultraviolet radiation and preferably UV-A radiation. The polymerization conditions obviously depend on the monomers used in the compositions.

Such polymerization processes are described, inter alia, in patent FR-A-2,699,541.

Thus, the polymerizable compositions according to the invention generally also contain polymerization initiators, preferably photoinitiators, in proportions of from 0.001 to 5% by weight relative to the total weight of the composition, and even more preferably from 0.01 to 1%.

The photoinitiators which can be used in the polymerizable compositions according to the invention are, in particular, 2,4,6-trimethylbenzoyldiphenylphosphine oxide, 1-hydroxycyclohexyl phenyl ketone, 2,2-dimethoxy-1,2-diphenyl-1-ethanone and alkylbenzoin ethers.

The recommended photoinitiators are 1-hydroxycyclohexyl phenyl ketone and 2,4,6-trimethylbenzoyldiphenylphosphine oxide.

The polymerizable compositions according to the invention can also contain additives used conventionally in polymerizable compositions intended for moulding optical and ophthalmic articles, in particular contact lenses, in standard proportions, namely, inhibitors, dyes, UV absorbers, fragrances, deodorants, antioxidants and anti-yellowing agents.

The present invention also relates to transparent polymer compositions obtained by polymerization, and in particular by photopolymerization, of the polymerizable compositions described above.

The polymerization is carried out in a known manner, using an initial mixture containing the various monomers of the polymerizable composition and the optional adjuvants, the polymerization reaction being catalysable using catalysts such as benzoyle peroxide, cyclohexyl peroxydicarbonate, diisopropyl peroxydicarbonate or 2,2'-azobisbutyronitrile.

Preferably, the polymerization is a photopolymerization and, in this case, the polymerizable compositions according to the invention generally contain photoinitiators as indicated above.

Preferably also, this photopolymerization is a photopolymerization by irradiation with ultraviolet light.

The invention also relates to optical and ophthalmic articles manufactured from the transparent polymer compositions according to the invention, and in particular contact lenses.

The polymerizable compositions according to the invention can lead to the production of thermoplastic polymers. In this case, the polymerizable compositions are particularly suitable for obtaining optical and ophthalmic articles by injection-moulding (i.e. by compression, in a mould, of the polymerizable composition brought to a temperature above its glass transition temperature or to the melting point).

However, the compositions according to the invention can be used to obtain optical and ophthalmic articles by any standard moulding process.

In particular, lenses can be obtained in the final form by casting the polymerizable compositions between two moulds having the required surface geometry, followed by polymerization. A lens whose two faces are in their final state is thus obtained. Semi-finished lenses can also be manufactured having, after moulding, only one face in its final geometry, it being possible for the second face then to be surfaced as required.

EXAMPLE OF THE PREPARATION OF THE TRANSPARENT POLYMER ACCORDING TO THE INVENTION

The monomer is prepared in the absence of ultraviolet light.

An initiator is added to the monomer in a proportion of 0.1% by weight. This solution is then injected into the polymerization mould.

Polymerization is then carried out by ultraviolet radiation.

Monitoring of the polymerization kinetics is carried out using a near-infrared spectrometer which makes it possible to observe the disappearance of the acrylic C=C peak at 6200 cm$_{-1}$ for the methacrylic esters and at about 6140 cm$^{-1}$ for the methacrylic thioesters.

Homopolymerization of the methacrylic ester of 1,4-dithiacycloheptane could be achieved under good conditions, and the characteristics of the monomer and of the polymer are given below.

MONOMER: methacrylic ester of 1,4-dithiacycloheptane.

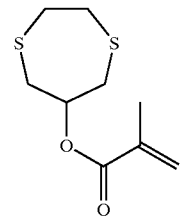

Properties: $n_D^{20} = 1.5447$
Abbe $n^b = 39.5$
transparent liquid stabilized with bis-di-tert-butylhydroxytoluene Homopolymerization in the presence of 0.1% initiator.
Near-infrared monitoring of kinetics.

Properties: $n_D^{20} = 1.5892$
Abbe $n^b = 43.5$
Yellow, brittle
$d = 1.24$

What is claimed is:

1. Polymerizable composition comprising at least one monomer of mono(thio) (meth)acrylate or di(meth)acrylate type bearing a 5- to 8-membered heterocycle consisting of C, H and S atoms and containing 2 or 3 endocyclic sulphur atoms, the heterocycle optionally being fused to a substituted or unsubstituted $C_5$–$C_8$ aromatic or $C_6$–$C_7$ polycyclanic ring.

2. Polymerizable composition according to claim 1, wherein the heterocycle is 6-membered.

3. Polymerizable composition according to claim 1, wherein the monomer has a molar mass of between 150 and 400.

4. Polymerizable composition according to claim 1, wherein the monomer has a molar mass between 150 and 350.

5. Polymerizable composition according to claim 1, wherein the monomer has a molar mass between 200 and 300.

6. Polymerizable composition according to claim 1, wherein the heterocycle contains two endocyclic sulphur atoms in positions 1–3 of 1–4 of the heterocycle.

7. Polymerizable composition according to claim 1, wherein the heterocycle contains three endocyclic sulphur atoms.

8. Polymerizable composition according to claim 1, wherein the monomer is thio(meth)acrylate.

9. Polymerizable composition, comprising at least one monomer of the formula:

(A)

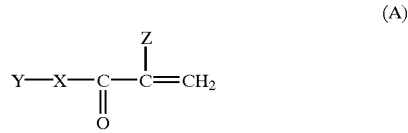

in which Z represents H or $CH_3$ and X represents O or S, and when X represents S, Y is a radical of formula:

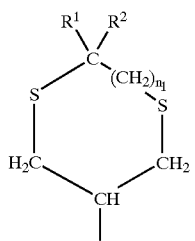
(a)

where $R^1$ and $R^2$ are chosen from H, alkyl radicals, or alternatively $R^1$ and $R^2$ together form a $-(CH_2)_5-$ radical and $n_1$ is an integer from 0 to 2 inclusive, and when X represents O, Y is the radical (a) defined above or a radical chosen from the radicals of formulae:

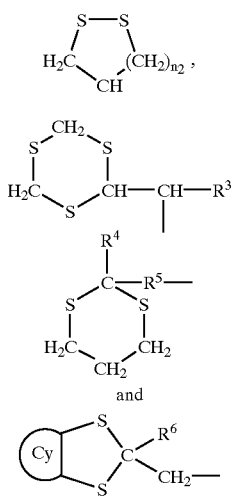

(b)

(c)

(d)

and (e)

which $n_2$ is an integer equal to 1 or 2, $R^3$ represents H or an alkyl group, $R_4$ represents H, an alkyl group or an aryl group; and $R^5$ is a divalent radical chosen from the groups of the following formulae:

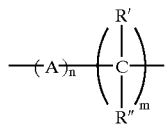
(I)

in which:

A denotes an aryl group, or an alkyl group, R and R″ denote, independently of each other, H, an alkyl group, aryl, or R' or R″ can be a group

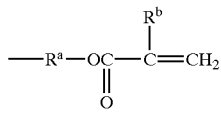

where $R^a$ is an alkylene group, and $R^b$ is H or $CH_3$, n takes the values 0 or 1 and $0 \leq m$ (integer $\leq 4$), and

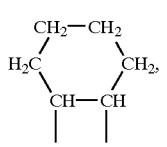
(II)

and $R^6$ denotes H or a methyl group, and Cy denotes a substituted or unsubstituted aryl ring.

10. Composition of claim 9 wherein $R^5$ is a divalent radical chosen from:

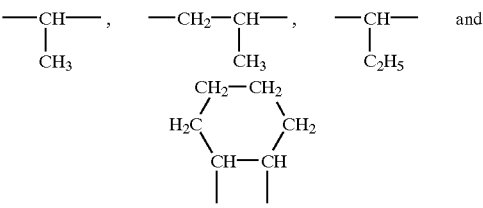

and Cy is a phenyl, tolyl or norbornyl group.

11. Composition of claim 10, wherein the monomer is chosen from the compounds of formulae:

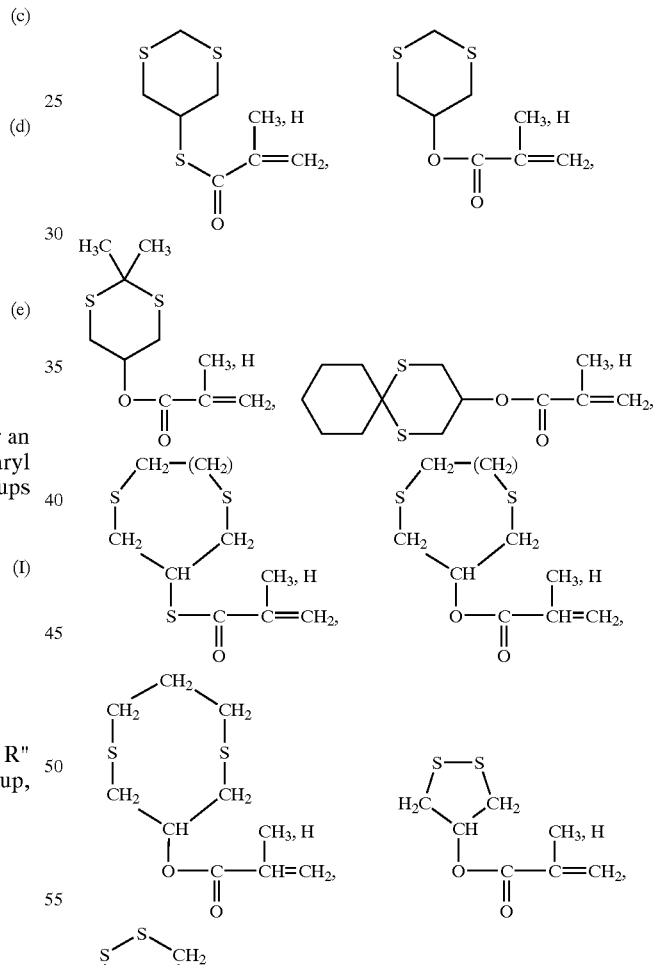

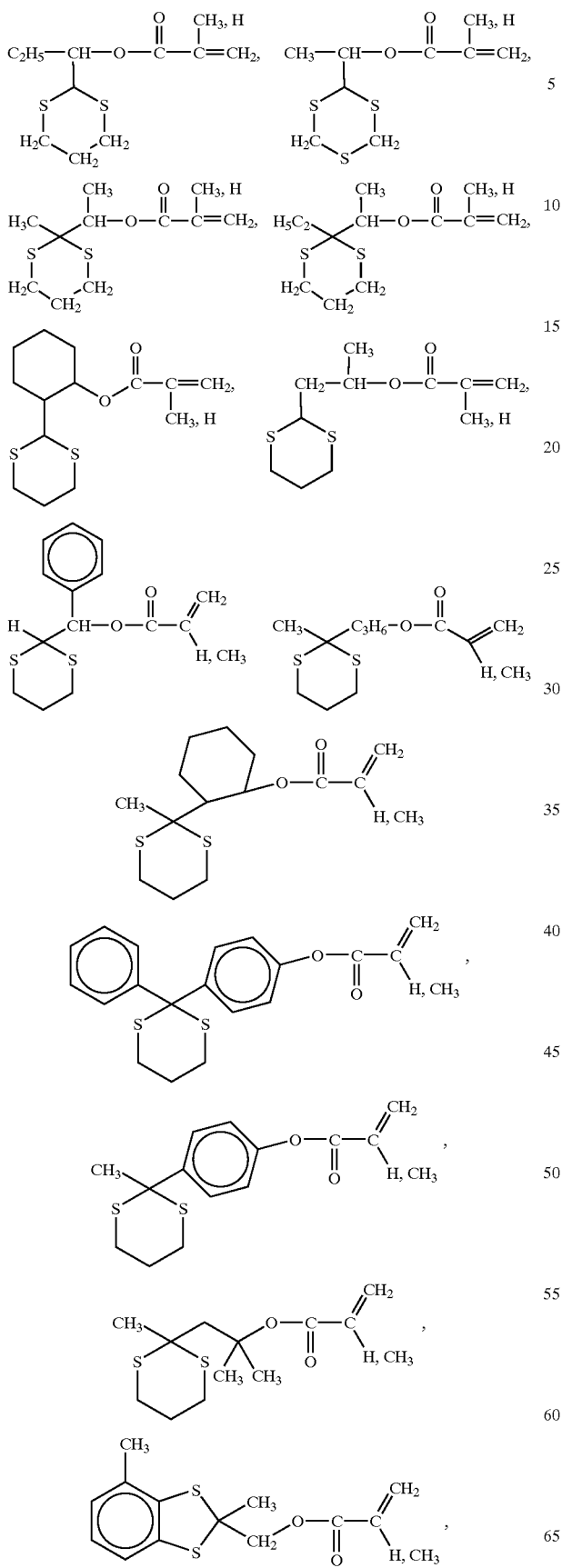
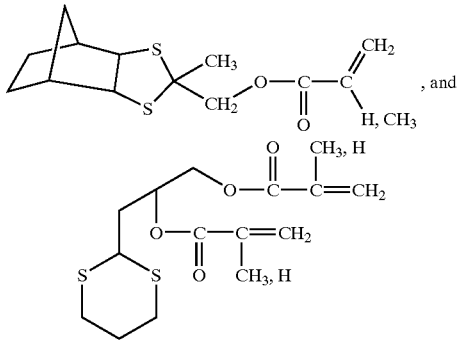

12. Composition of claim 9, wherein the alkyl groups represented by $R^1$, $R^2$, $R^3$ and $R^4$ are $C_1$–$C_4$ alkyl groups.

13. Composition of claim 12, wherein the alkyl groups represented by $R^1$, $R^2$, $R^3$ and $R^4$ are a methyl or ethyl group.

14. Composition of claim 9, wherein the alkyl groups represented by A, R' and R" are $C_1$–$C_6$ alkyl groups.

15. Composition of claim 9, wherein the phenyl groups represented by $R^4$, A, R' and R" are $C_6$–$C_{12}$ aryl groups.

16. Composition of claim 15, wherein the phenyl groups represented by $R^4$, A, R' and R" are phenyl groups.

17. Composition of claim 9 wherein $R^a$ is a $C_1$–$C_6$ alkylene group.

18. Composition of claim 17 wherein $R^a$ is a —$CH_2$— group.

19. Composition of claim 9 wherein Cy is a phenyl, tolyl or norbornyl group.

20. Polymerizable composition according to claim 9, further comprising one or more comonomers other than the monomers of formula (A).

21. Polymerizable composition according to claim 20, wherein the comonomer(s) is (are) chosen from vinyl, acrylic or methacrylic monomers and allylcarbonates of linear or branched, aliphatic or aromatic liquid polyols.

22. Polymerizable composition according to claim 1, further comprising a polymerization initiator.

23. Polymerizable composition according to claim 22 wherein the polymerization initiator is a photopolymerization initiator.

24. Polymerizable composition according to claim 23, wherein the photoinitiator is chosen from 2,4,6-trimethyl-benzoyldiphenylphosphine oxide, 1-hydroxycyclohexyl phenyl ketone, 2,2-dimethoxy-1,2-diphenyl-1-ethanone and alkylbenzoin ethers, and mixtures thereof.

25. Transparent article resulting from the polymerization of the polymerizable composition according to claim 1.

26. Transparent article resulting from the photopolymerization of the polymerizable composition according to claim 23.

27. Optical or ophthalmic article obtained by moulding and polymerization of a composition according to claim 1.

28. Ophthalmic article according to claim 27, characterized in that the article is an ophthalmic lens.

29. Polymerizable composition according to claim 9 wherein $R^1$ and $R^2$ are $C_1$–$C_4$ alkyl radicals.

30. Polymerizable composition according to claim 9 wherein $R^1$ and $R^2$ are a $CH_3$ radical.

* * * * *

UNITED STATES PATENT AND TRADEMARK OFFICE
CERTIFICATE OF CORRECTION

PATENT NO. : 6,472,488 B2
DATED : October 29, 2002
INVENTOR(S) : Caye et al.

It is certified that error appears in the above-identified patent and that said Letters Patent is hereby corrected as shown below:

<u>Column 42,</u>
Line 17, please delete "norbomyl" and insert -- norbornyl --.

<u>Column 44,</u>
Line 33, please delete "norbomyl" and insert -- norbornyl --.

Signed and Sealed this

Fourth Day of February, 2003

JAMES E. ROGAN
*Director of the United States Patent and Trademark Office*